(12) United States Patent
Hood et al.

(10) Patent No.: US 7,981,442 B2
(45) Date of Patent: Jul. 19, 2011

(54) ULTRASOUND ENHANCEMENT OF DRUG RELEASE ACROSS NON-IONIC SURFACTANT MEMBRANES

(75) Inventors: Elizabeth Hood, Tampa, FL (US); Joel A. Strom, Tampa, FL (US); Michael VanAuker, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/427,034

(22) Filed: Jun. 28, 2006

(65) Prior Publication Data

US 2006/0292211 A1 Dec. 28, 2006

Related U.S. Application Data

(60) Provisional application No. 60/695,484, filed on Jun. 28, 2005.

(51) Int. Cl.
*A61K 9/127* (2006.01)
*A61K 9/48* (2006.01)

(52) U.S. Cl. ............... 424/450; 424/78.03; 424/401; 424/486; 514/2; 514/44

(58) Field of Classification Search ............ 424/9.51, 424/9.52, 450, 465, 455, 489; 514/937, 44; 210/649–652, 646, 204, 152

See application file for complete search history.

(56) References Cited

U.S. PATENT DOCUMENTS

| | | | |
|---|---|---|---|
| 4,780,212 A * | 10/1988 | Kost et al. ............... | 210/646 |
| 5,580,575 A | 12/1996 | Unger et al. | |
| 6,403,056 B1 * | 6/2002 | Unger ..................... | 424/9.51 |
| 6,623,430 B1 | 9/2003 | Slayton et al. | |
| 6,884,407 B1 | 4/2005 | Unger | |
| 7,169,382 B2 * | 1/2007 | Chopart et al. ............ | 424/78.03 |
| 2003/0064097 A1 * | 4/2003 | Patel et al. ................ | 424/465 |
| 2003/0157025 A1 * | 8/2003 | Unger et al. .............. | 424/9.52 |
| 2005/0019266 A1 | 1/2005 | Unger | |

OTHER PUBLICATIONS

Elizabeth Hood, Monica Gonzalez, Joel strom and Michael VanAuker, Ultrasound Enhancement of Drug Release Across Non Ionic Surfactant Vesicle Membranes, Procedings of the 26th Annual International Conference of the IEEE EMBS San Francisco, CA, USA Sep. 1-5, 2004.*

Ijeoma F. Uchegbu and Suresh P. Vyas, Non-ionic surfactant based vesicles (niosomes) in drug delivery, International Journal of Pharmaceutics, 172, 33-70, 1998.*

Ka-Yun Ng, Yang Liu, Therapeutic Ultrasound: Its Application in Drug Delivery, Medicinal Research Reviews, vol(2), 204-223, 2002.*

Hamilton AJ, Huang SL, Warnick D, Rabbat M, Kane B, Nagaraj A, Klegerman M, McPherson DD. Intravascular ultrasound imaging of atheroma components in vivo. J Am Coll Cardiol 2004:43:453-60.

Tiuknihoy SD, Khan AA, Huang S, Klegerman ME MacDonald RC, McPherson DD. Novel Echogenci drug-immunoliposomes for drug deliver. Invest Radiol 2004;39;104-110.

Unger EC, Porter T, Culp W, Labell R, Matsunaga T, Zutshi R. Therapeutic applications of lipid-coated microbubbles. Advanced Drug Delivery Reviews 2004;56:1291-1314.

Price RJ, Kaul S. Contrast ultrasound targeted drug and gene delivery; an update on a new therapeutic modalility. J Cardiovase Pharmacol Therapeuti 2002;7:171-180.

Tachibana K, Tachibana S. Albumin microbubble echo-contrast material as an enhancer for ultrasound accelerated thrombolysis. Circulation 1995;95:1148-50.

Villanueva FS, Jankowski RJ, Klibanov S, Pina ML, Alber SM, Watkins SC, Brandenburger GH, Wagner WR, Microbubbles targeted to intercellular adhesion molecule-I bind to activated coronary artery endothelial cells. Circulation 1998;98;1-5.

VisualSonics Vevo 770 Ultrasound. Cell and Tissue Analysis Core. http://ctac.mbi.ufl.edu/VisSon.htm.

Mitragotri, S. Healing Sound: The Use of Ultrasound in Drug Delivery and Other Therapeutic Applications. Nature Reviews. Mar. 2005. vol. 4. pp. 255-260.

* cited by examiner

*Primary Examiner* — Michael G Hartley
*Assistant Examiner* — Jagadishwar R Samala
(74) *Attorney, Agent, or Firm* — Michele L. Lawson; Smith & Hopen, P.A.

(57) ABSTRACT

A method of targeted drug delivery and imaging using nonionic surfactant vesicles (niosomes) in combination with ultrasound. Niosomes have potential applications in targeted drug delivery and imaging because of their ability to encapsulate therapeutic agents and their enhanced uptake by physiological membranes. Ultrasound may be used to mediate delivery non-invasively by altering the niosome membrane structure. Niosomes composed of polyoxyethylene sorbitan monostearate (Tween 61), cholesterol, and dicetyl phosphate were synthesized via a thin film hydration technique and used for encapsulation studies. Carboxyfluorescein dye (CF) was used as a drug model to demonstrate delivery. The amount of dye in the niosomes, the concentration of the vesicles, and their mean particle size after each 5 minute incremental exposure to ultrasound was monitored. Dye concentration in niosome samples decreased while the population and size distribution of the niosome remained largely unchanged. Ultrasound is demonstrated to enhance the rate of dye diffusion across the niosome membrane non-destructively.

8 Claims, 5 Drawing Sheets

ULTRASOUND ENHANCEMENT OF DRUG RELEASE ACROSS NON-IONIC SURFACTANT MEMBRANES

CROSS REFERENCE TO RELATED APPLICATIONS

This application claims priority to currently pending U.S. Provisional Patent Application 60/695,484, entitled, "Ultrasound Enhancement of Drug Release Across Non-Ionic Surfactant Membranes", filed Jun. 28, 2005, the contents of which are herein incorporated by reference.

FIELD OF INVENTION

This invention relates to the field of therapeutic drug delivery. More specifically, this invention relates niosomes comprising therapeutic compounds delivered to a targeted region of a patient using ultrasound.

BACKGROUND OF THE INVENTION

Drug delivery systems are developed to lower therapeutic doses, increase residence time, and prolong release over time of drugs to targeted tissues. Toxic effects of drugs can be minimized when uptake by untargeted organs is reduced. Targeting allows delivery of relatively high levels of drug to a focal site, minimizing systemic complications and lowering costs of therapy. Liposomes are self assembly vesicles made from phospholids and cholesterol that have been widely used in targeted drug delivery applications including cancer therapy, gene delivery, and thrombolysis (Lasic, D. D., *Liposomes: From Physics to Applications*. Amsterdam, the Netherlands: Elsevier, 1993, pp 31-32.) since their discovery almost forty years ago (Bangham, A. D. et al., "Diffusion of univalent ions across the lamellae of swollen phospholipids," J. Mol. Bio. vol. 13, pp. 238-252, 1965.). Vesicles made from synthetic non ionic surfactants (niosomes) are analogous to liposomes. Niosomes have also been used as drug encapsulating vesicles showing advantages over liposomes, including greater chemical stability, lower cost, easier storage and handling, and less potential for toxicity (Uchegbu, I. F. et al., "Non-ionic surfactant vesicles (niosomes): physical and pharmaceutical chemistry." Adv. Colliod. Interfac., vol. 58, no. 1, pp. 1-55, 1995.). As drug delivery vesicles, niosomes have been shown to enhance absorption of some drugs across cell membranes (Lasic, D. D., 1993, pp 31-32), to localize in targeted organs (Jain, C. P. et al., "Preparation and characterization of niosomes containing rifampicin for lung targeting," Microencapsulation, vol. 12 no. 4, pp. 401-407, 1995; Namdeo, A. J. et al., "Niosomal delivery of 5-fluoruoracil," J. Microencapsulation, vol. 16, no. 6, pp. 731-740, 1999.) and tissues (Baille, A. J. et al., "Non-ionic surfactant vesicles, niosomes, as delivery system for the anti-leishmanial drug, sodium stribogluconate," J. Pharm. Pharacol., vol. 38, pp. 502-505, 1986; Azmin, M. N., et al., "The effect of non-ionic surfactant vesicle (niosome) entrapment on the absorption and distribution of methotrexate in mice," J. Pharm. Pharmacol., vol. 37, pp. 237-242, 1985.), and to elude the reticuloendothelial system (Gopinath, D. et al., "Pharmocokinetics of zidovudine following intravenous bolus administration of a novel niosome preparation devoid of cholesterol.," A. F. Drug Research, vol. 51, no. 11, pp. 924-930. November, 2001).

Ultrasound enhanced drug delivery has several important advantages in that it is noninvasive, can be carefully focused and controlled and can penetrate deep into the body. Early uses of ultrasound to aid drug delivery were transcutaneous. The technique for using ultrasound to drive drug molecules across the percutaneous barrier to a targeted area, or 'phonophoresis', was developed fifty years ago, and is itself a field of research (Ng, K. et al., "Therapeutic ultrasound: its application in drug delivery," Med. Res. Rev., vol. 22, no. 2, pp. 204-223, 2002.). Other drug therapies shown to be enhanced by ultrasound include chemotherapy, thrombolytics, and gene delivery. Drug targeting and localized release has been shown to enhance uptake by tumor cells when encapsulated by polymeric micelles subjected to focused ultrasound at therapeutic levels (Rapoport, N.Y. et al., "Ultrasound-triggered drug targeting of tumors in vitro and in vivo," Ultrasonics, vol. 42, pp. 943-950, 2004). Low intensity ultrasound has been shown to enhance the permeabilization of liposomes with polyethylene glycol head groups (Lin, H. Y. et al., "PEG-Lipids and oligo(ethylene glycol) surfactants enhance the ultrasonic permeabilizability of liposomes," Langmuir, vol. 19, pp. 1098-1105, 2003; Baillic, A. J., et al., "The preparation and properties of niosome—non-ionic surfactant vesicles," J. Pharm. Pharmacol., vol. 37, pp. 863-868, 1985.).

Effective targeted drug delivery can be achieved in many instances through release of therapeutic agents in a more controlled manner than possible with passive diffusion across a bilayer membrane. Controlled release of a drug from a specifically targeted vesicle to a site using ultrasound can be optimized through the tuning of transducer frequency, beam distance and focus, and absolute and peak power delivered to the vesicle suspension. The lipid bilayers that make up liposomes and niosomes are similar to biological membranes in that they are able to self-repair when perturbed. Sonication is widely used to reduce large multilamellar vesicles to smaller unilamellar ones. Control of membrane permeability via ultrasound would have many therapeutic applications especially when coupled with the active and passive drug targeting possible with lipid membrane vesicles. To this end, a technique for making non ionic surfactant vesicles and the use and effect of exposure to clinical levels of ultrasound to achieve release of the drug model is taught herein.

SUMMARY OF INVENTION

The present invention provides a method for the targeted delivery of a pharmaceutical compound to a region of a patient. The method includes the steps of providing a niosome containing the compound, administering an effective amount of the niosome to the patient and inducing the dispersion of the niosome membrane using ultrasound to release the compound in the targeted region to achieve therapeutic effect. In certain aspect the method can include the step of monitoring the niosomes using ultrasound to determine the presence of the niosome in the target region. The compound can be a therapeutic compound or a diagnostic compound. In certain aspect of the invention the niosome comprises polyoxyethylene sorbitan monostearate (Tween 61), cholesterol and dicetyl phosphate. The polyoxyethylene sorbitan monostearate (Tween 61) and the cholesterol can be present in about equimolar combination. The method of claim 1 wherein the niosome can be synthesized using a thin film hydration methodology.

In an aspect of the present invention there is a catheter equipped with both an intravascular ultrasound imaging probe and a port for injection of the niosomes. Intravascular ultrasound provides detailed imaging of the interior surfaces of the arterial wall, allowing for visualization of the atherosclerotic plaque. This allows for guided delivery of the niosome. When a plaque is found, the niosomes are injected through the port. This allows for the delivery of a high concentration of the particles targeted to a focused site. This will improve uptake relative to similar particles that are delivered through the intravenous injection. The injected niosomes will then adhere to the diseased endothelium by the use of the antibody/ligand interaction. After adhesion, the ultrasound will be "tuned" to facilitate release of drug at the location of the plaque. This will reduce doses required for efficacy relative to intravenous or oral administration with non-specific uptake.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
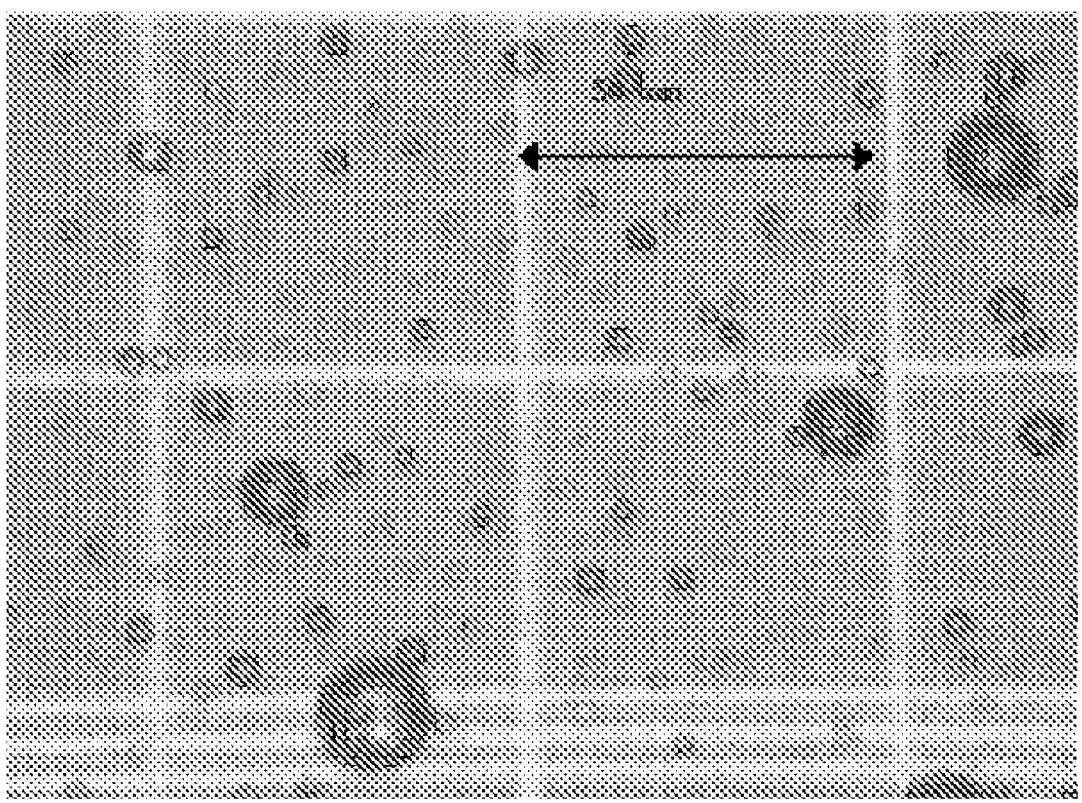
FIG. 1 is a micrograph of a niosome sample on a hemocytometer. Arrow length indicates 50 μm.

A method of targeted drug delivery and imaging using nonionic surfactant vesicles (niosomes) in combination with ultrasound. Niosomes have potential applications in targeted drug delivery and imaging because of their ability to encapsulate therapeutic agents and their enhanced uptake by physiological membranes. Ultrasound may be used to mediate delivery non-invasively by altering the niosome membrane structure. Niosomes composed of polyoxyethylene sorbitan monostearate (Tween 61), cholesterol, and dicetyl phosphate were synthesized via a thin film hydration technique and used for encapsulation studies. Carboxyfluorescein dye (CF) was used as a drug model to demonstrate delivery. The amount of dye in the niosomes, the concentration of the vesicles, and their mean particle size after each 5 minute incremental exposure to ultrasound was monitored. Dye concentration in niosome samples decreased while the population and size distribution of the niosome remained largely unchanged. Ultrasound is demonstrated to enhance the rate of dye diffusion across the niosome membrane non-destructively.

Methods

Niosomes were synthesized using a thin film hydration technique (Baillie, A. J., et al., "The preparation and properties of niosome-non-ionic surfactant vesicles," J. Pharm. Pharmacol., vol. 37, pp. 863-868, 1985.) with the surfactant polyoxyethylene sorbitan monostearate (Tween 61), cholesterol, and dicetyl phosphate (DCP) in a 1.00:1.00:0.105 molar ratio. The capability of niosomes of made from several different sorbitan monoesters (Span 20, 40, 60) has been studied and the ability of each to encapsulate a fluorescent dye, 5(6)-carboxyfluorescein (CF) used as a drug model has been evaluated (Hood, E. et al., "Entrapment efficiency and membrane permeability of non ionic surfactant vesicles," in Proc. 2003 AIChE Annual Conference Proceeding CD-ROM, San Francisco, Calif.). The surfactant Tween 61 is similar to Span 60, sharing a common stearyl chain tail group ($C_{18}$) but having more highly hydrated polyoxyethylene (PEO) groups on the hydrophilic group. Tween 61, in equimolar combination with cholesterol, has been reported to have greater encapsulation capabilities of aqueous solutions, and greater stealth in vivo due to the high level of hydration on the vesicle surface (Manosroi, A. et al., "Characterization of vesicles prepared with various non-ionic surfactants mixed with cholesterol." Colliod Surface B, vol. 30, pp. 129-138, 2003.). Niosomes were synthesized using a thin film hydration method followed by sonication. Once the thin films were hydrated in a 5.0 mM CF solution the niosomes were separated from the unencapsulated dye and any unformed lipids or micelles using gel exclusion chromatography with an Amersham ÄKTAprime™ fraction collection system with UV monitoring coupled with a 120 ml column filled with Sephadex G50. In this process, the niosome sample is passed through a column packed with porous gel beads of a uniform pore size (Sephadex G50 pore size 50 nm) using phosphate buffer solution (PBS) as the carrier liquid. The larger vesicle particles fall through the voids and are eluted early while the smaller particles such as unencapsulated dye and unformed lipids are caught up in the pores of the beads, traveling through the column more slowly. This technique allows sample separation into fractions by particle size.

Niosome Characterization Methods

Niosome particle analysis included light scattering, single particle optical sensing technology, optical microscopy, and fluorescence measurements. Fluorescence changes were measured to evaluate encapsulation by the vesicles and leakage of dye from the vesicles over time. Mean particle size and concentration of the niosome vesicles was determined by light scattering and light obstruction techniques using a Particle Sizing Systems Accusizer 780™ with a lower diameter detection limit of 0.57 μm. The entrapment capability and membrane permeability were measured by disrupting the vesicles with Triton X 100, a non-fluorescing surfactant, and quantifying the signal change before and after vesicle breaking using a Perkin Elmer™ spectrometer. Entrapment of CF was determined using fluorescence absorbance correlated to a standard curve of concentration versus intensity. Initial readings of niosome solutions are described as background intensities in this discussion, and final readings include the CF released from the lysed niosomes. The difference of the two gives the dye entrapped in the niosome suspensions. All readings are related to the calibration curve and are reported in moles of CF.

Experimental Methods

Niosome suspensions of mean particle size 0.89 μm and 1.05 μm were subjected to 5 minute increments of ultrasound, with a sample of each left unperturbed as a control. An Acuson Aspen™ echocardiography machine coupled to a 4V2c transducer delivered ultrasound to static suspensions of several ml for each sample. Machine settings were kept constant throughout the experiment with the frequency set to 3.5 MHz, the dynamic range set to 70 dB, and the initial gain set to 10 dB. The spatial peak temporal average was 46 mW/cm$^2$, and the total absolute power was 65 mW.

Fluorescence readings of the niosomes and suspending fluid were obtained at 5 min increments over 15 minutes of ultrasound exposure. All vesicle characterization measurements were repeated three times.

Results

Figure 2:
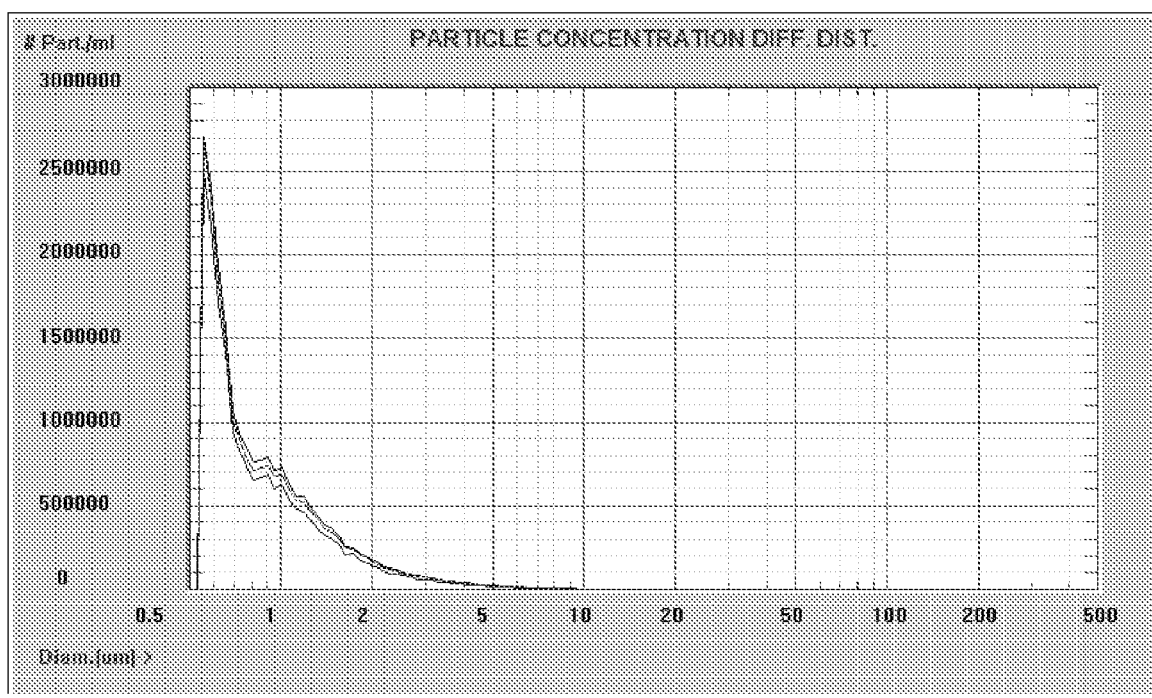
FIG. 2 is a graph illustrating particle size distributions of the 1.05 μm control sample over the duration of the experiment. Upper line plot=0 min, middle line plot=5 min, lower line plot=10 min and 15 mins (note that plots for 10 and 15 mins are superimposed and not distinguishable in the graph).

Vesicle formation is verified using light microscopy as shown in FIG. 1. The graph shown in FIG. 2. represents the particle size distributions (PSD) of the control samples over the duration of the experiment. The CF in the control samples remain unchanged over the duration of the experiment.

Figure 3:
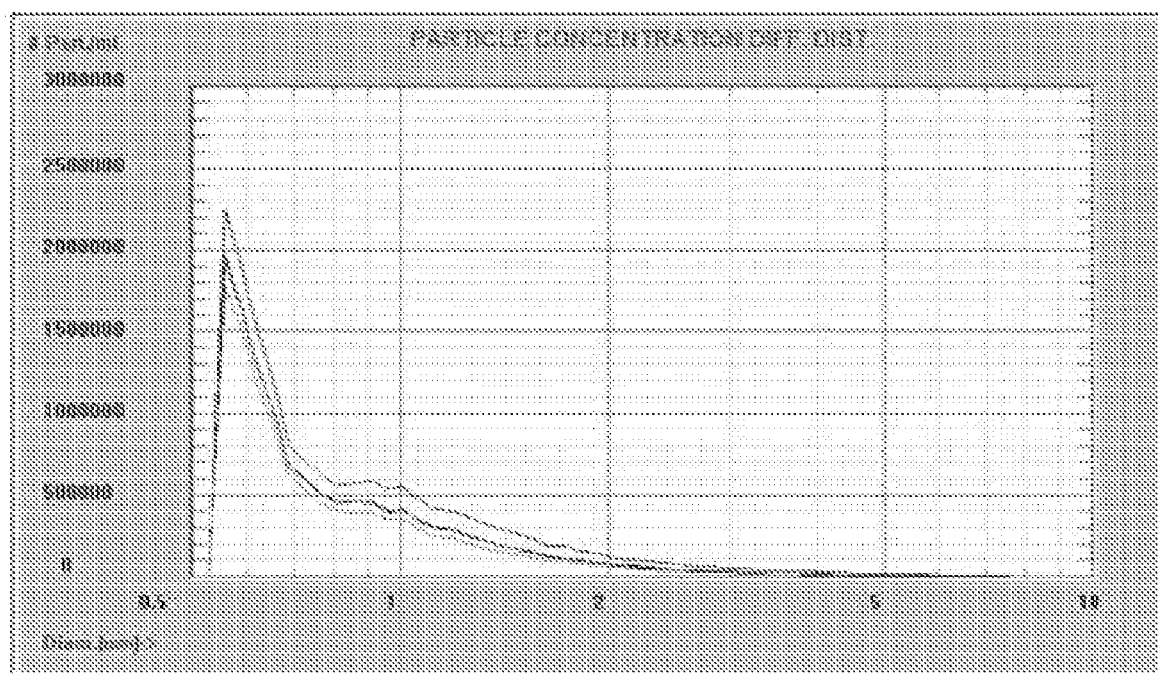
FIG. 3 is a graph illustrating particle size distributions (PSD) of the 1.05 μm sample over the duration of the experiment. Each curve represents a PSD at a given ultrasound exposure time.
Figure 4:
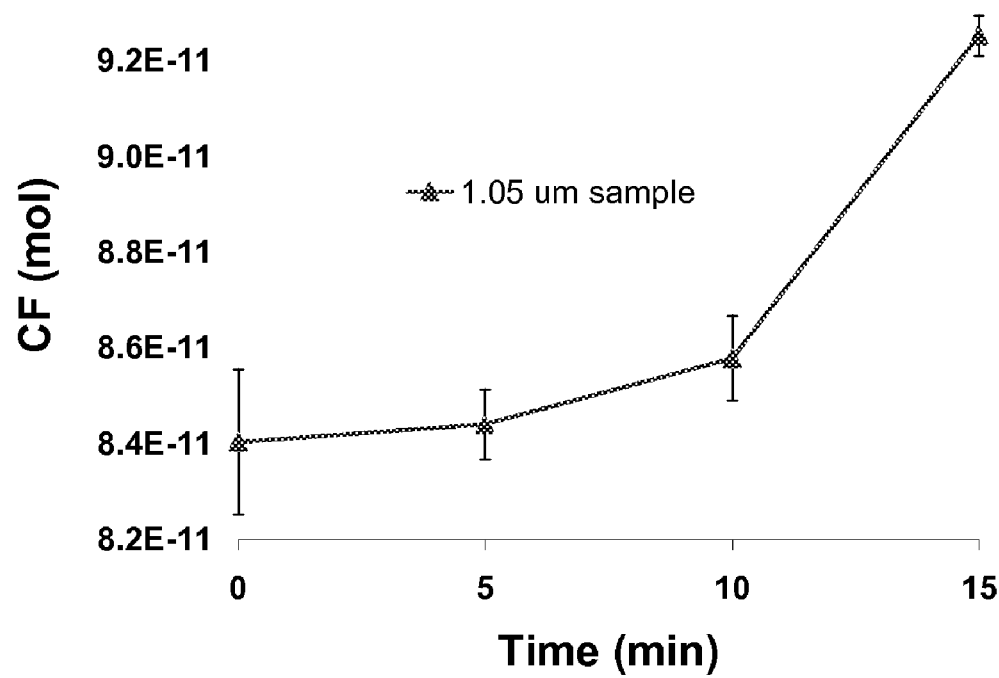
FIG. 4 is a graph illustrating free CF (mol) in solution over ultrasound exposure time in the 1.05 mm sample. Error bars represent standard error of the mean.
Figure 5:
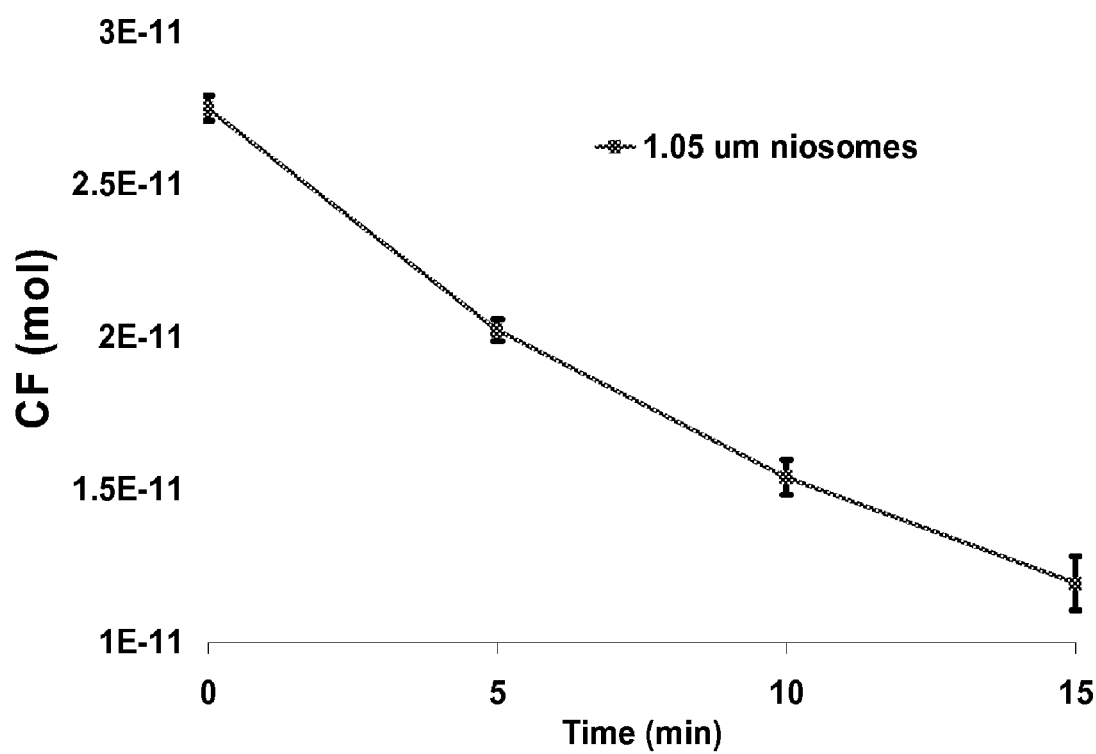
FIG. 5 is a graph illustrating encapsulated CF (mol) in 1.05 niosomes over ultrasound exposure time.

In FIG. 3 the PSD of the niosome sample exposed to ultrasound is shown. The slight downward shifts of the curves with successive sample measurements indicate the decrease in the overall counts over the exposure time. The overall decrease in particle counts with exposure to ultrasound in the sample was 13% as calculated by the change in total particles measured. The graph in FIG. 4 shows an increase in the CF in the suspending solution. The magnitude of this increase is greater than the relatively small shift of overall particle concentration shown in the PSD of the same sample. FIG. 5 shows the decrease in encapsulated CF with ultrasound exposure time.

Discussion

Release of CF from the niosomes after exposure to ultrasound is evidenced by the two fold decrease in encapsulated CF and the nearly 10% increase of dye measured in the suspending solution. The PSD of the vesicles shows that significant release took place with relatively low destruction of vesicles. These data support the principle that clinical levels of ultrasound may be used to disrupt the membranes of encapsulating drug vesicles and allow control of destruction and release. Studies of the exposure of non ionic surfactant vesicles to clinical levels of ultrasound showed enhanced release of encapsulated materials without corresponding levels of vesicle destruction.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the targeted delivery of a pharmaceutical compound to a region of a patient comprising the steps of:
   providing a niosome comprising the compound;
   administering to the patient an effective amount of the niosome; and
   inducing substantially nondestructive niosome membrane permeabilization and controlled release of the compound in the targeted region by exposing vesicles to clinical levels of ultrasound at a frequency of about 3.5 MHz wherein release is controlled by adjusting transducer frequency, beam distance and focus, absolute power and peak power.

2. The method of claim 1 further comprising the steps of monitoring the niosomes using ultrasound to determine the presence of the niosome in the target region.

3. The method of claim 1 wherein the compound is a therapeutic compound.

4. The method of claim 1 wherein the compound is a diagnostic compound.

5. The method of claim 1 wherein the niosome comprises polyoxyethylene sorbitan monostearate (Tween 61), cholesterol and dicetyl phosphate.

6. The method of claim 5 wherein the polyoxyethylene sorbitan monostearate (Tween 61) and the cholesterol are present in about equimolar combination.

7. The method of claim 6 wherein the niosomes are synthesized in about 1.00:1.00:0.105 molar ratio for polyoxyethylene sorbitan monostearate (Tween 61):cholesterol:dicetyl phosphate.

8. The method of claim 1 wherein the niosome is synthesized using a thin film hydration methodology.

* * * * *